(12) United States Patent
Ooshima et al.

(10) Patent No.: US 6,784,919 B2
(45) Date of Patent: Aug. 31, 2004

(54) ORAL CAVITY IMAGE PICKUP APPARATUS

(75) Inventors: Kiyoko Ooshima, Shijonawate (JP); Shinji Uchida, Neyagawa (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 378 days.

(21) Appl. No.: 09/770,817

(22) Filed: Jan. 26, 2001

(65) Prior Publication Data

US 2001/0010538 A1 Aug. 2, 2001

(30) Foreign Application Priority Data

| Jan. 27, 2000 | (JP) | 2000-019232 |
| Jan. 31, 2000 | (JP) | 2000-022851 |

(51) Int. Cl.[7] .............................................. H04N 7/18
(52) U.S. Cl. ......................................................... 348/66
(58) Field of Search .............................. 348/61, 66–70, 348/77; 396/16, 21, 155; 433/29, 71; 600/104, 590; H04N 7/18

(56) References Cited

U.S. PATENT DOCUMENTS

| 3,382,781 A | | 5/1968 | Hamilton |
| 3,812,505 A | * | 5/1974 | Elliott ......................... 396/16 |
| 4,104,530 A | | 8/1978 | Weiss |
| 4,915,626 A | * | 4/1990 | Lemmey ....................... 348/66 |
| 5,016,098 A | * | 5/1991 | Cooper et al. ................ 348/66 |
| 5,051,823 A | * | 9/1991 | Cooper et al. ................ 348/66 |
| 5,143,086 A | | 9/1992 | Duret et al. |
| 5,251,025 A | * | 10/1993 | Cooper et al. .............. 600/104 |
| 5,429,502 A | * | 7/1995 | Cooper et al. ................ 348/66 |
| 5,458,487 A | * | 10/1995 | Komatsu et al. ............ 600/590 |
| 5,745,165 A | | 4/1998 | Atsuta et al. |
| 5,857,853 A | | 1/1999 | Van Nifterick et al. |

FOREIGN PATENT DOCUMENTS

| EP | 0282832 | 9/1988 |
| EP | 0326497 | 8/1989 |
| FR | 674 647 | 1/1930 |
| JP | 8-332170 | 12/1996 |
| JP | 10-179516 | 7/1998 |
| JP | 11-275405 | 10/1999 |

* cited by examiner

Primary Examiner—Richard Lee
(74) Attorney, Agent, or Firm—RatnerPrestia

(57) ABSTRACT

An oral cavity image pickup apparatus having an image pickup device and a holding device including a first arm and a second arm. The first arm is of sufficient length for placement inside an oral cavity at least between left and right molars defining a transverse dimension. The image pickup device has an object lens and an imaging device and is held on at least the first arm between the first and second molars. The second arm has a first part for placement inside the oral cavity and coupled to the first arm. The second arm also has a second part at least as wide in transverse dimension as the first part for extending from both sides of the oral cavity. The image pickup device can image pick up full or partial dentition exposed inside and/or outside the oral cavity and partial bio-tissue at the same time.

22 Claims, 23 Drawing Sheets

ORAL CAVITY IMAGE PICKUP APPARATUS

BACKGROUND OF THE INVENTION

The present invention relates to an oral cavity image pickup apparatus to be utilized for observing the interior and/or exterior of an oral cavity in dental surgery.

Field of the Invention

In recent years, video-scope using CCD has been used for medical examination and treatment for a diseased part inside of an oral cavity. For such a video-scope, there are video-scope or the like which image-pick up one or a plurality of teeth by holding the tip end portion thereof from the outside of the oral cavity or inserting it into the oral cavity or the like as disclosed in Japanese Patent Laid-Open No. 8-332170.

In case of image-picking up the entire oral cavity including the dentition from the outside of the oral cavity to preserve the data, there is used a dentist's camera obtained by providing a photographing camera with annular illumination. In this case, the "inside of the oral cavity" means within space which spreads toward the throat with the upper and lower dentition a boundary, and the "outside of the oral cavity" means the inside and a portion toward the exterior of the lips with the upper and lower dentition a boundary.

A "8020 campaign" for holding 20 teeth at 80 years old has been promoted by the Ministry of Welfare or the like, and further emphasis has been placed on early detection and early treatment of decayed teeth. Also, recently our way of thinking has advanced from medical treatment to prevention, and this preventive examination and treatment start with grasping a patient's state of oral cavity. As their method, a photograph of the oral cavity is taken, and is preserved as a record.

Conventionally, in the dental surgery, a small-diameter dental mirror has been generally used on examining the state of the interior of the mouth, but in recent years, video-scope using a solid state imaging device such as CCD has been gradually utilized in informed consent or the like for observing and showing the patient an image on the monitor television for explanation.

In such a video-scope, according to the conventional technique disclosed in Japanese Patent Laid-Open No. 8-332170, the video-scope is used by holding it in one hand so as to facilitate an operation for locally photographing such as observation of one or a plurality of teeth.

In the case, however, where photographing is made in units of one tooth or a plurality of teeth, it takes time and it is difficult to identify which tooth within the dentition the tooth photographed is, and it is also difficult to pigeonhole the data.

When such an operation is made in the dental examination in health facilities and schools for infants and children, it is inefficient such as prolonged consultation hours or the like.

Further, the conventional dentist's camera photographs the entire oral cavity from just the front, and has the same form as an ordinary photographing camera, and therefore, teeth in the depths such as the molar are difficult to take a photograph because they are covered with the cheek portion.

SUMMARY OF THE INVENTION

The present invention has been achieved in the light of such problems, and is aimed to provide a simple and easy-to-use an intra-oral cavity image pickup apparatus for image-picking up the dentition and gums at a time from inside and/or outside the oral cavity.

One aspect of the present invention is an oral cavity image pickup apparatus, comprising:
  image pickup means having at least an object lens and an imaging device; and
  holding means of holding said image pickup means inside and/or outside an oral cavity,
wherein said image pickup means is capable of image-picking up full or partial dentition exposed inside and/or outside said oral cavity and partial bio-tissue at a time.

Another aspect of the present invention is an oral cavity image pickup apparatus, comprising:
  image pickup means having at least an object lens and an imaging device; and
  holding means of holding said image pickup means inside and/or outside an oral cavity,
  wherein said holding means has a bitten portion which is bitten by upper and lower teeth to thereby stabilize an entire apparatus, and
  said image pickup means is disposed inside and/or outside said oral cavity by said bitten portion of said holding means being bitten by said upper and lower teeth.

Still another aspect of the present invention is an oral cavity image pickup apparatus, comprising:
  a plurality of image pickup means having at least an object lens and an imaging device; and
  holding means of holding said image pickup means inside and/or outside an oral cavity,
wherein said plurality of imaging devices are disposed in such manner that such imaging device has different direction to each other.

Yet another aspect of the present invention is the oral cavity image pickup apparatus, wherein said image pickup means is capable of image-picking up at a time full or partial dentition belonging to an upper chin, and a portion of bio-tissue and/or full or partial dentition belonging to a lower chin, and a portion of bio-tissue.

Still yet another aspect of the present invention is the oral cavity image pickup apparatus according, wherein said object lens is a fish-eye lens.

A further aspect of the present invention is the oral cavity image pickup apparatus, wherein said holding means has light projecting means and said light projecting means projects a light upon full or partial dentition exposed within and/or without said oral cavity and partial tissue.

A still further aspect of the present invention is the oral cavity image pickup apparatus, wherein said holding means has dentition exposure means, and in a state in which said image pickup means is capable of image-picking up, at least a portion of said dentition exposure means is disposed at both end portions of lips in such a manner that said lips and a portion of the cheek are pushed open.

A yet further aspect of the present invention is the oral cavity image pickup apparatus, wherein said holding means has first holding means to be disposed inside said oral cavity, and second holding means to be disposed outside said oral cavity.

A still yet further aspect of the present invention is the oral cavity image pickup apparatus, wherein said first holding means and said second holding means are integrally fixed.

An additional aspect of the present invention is the oral cavity image pickup apparatus, wherein said first holding means and said second holding means are detachably disposed on said dentition exposure means.

A still additional aspect of the present invention is the oral cavity image pickup apparatus, wherein said image pickup means is movably disposed on said holding means.

A yet additional aspect of the present invention is the oral cavity image pickup apparatus, wherein said image pickup means is disposed on said first holding means and said first holding means is quasi-horse shoe shaped, U-character shaped or V-character shaped.

A still yet additional aspect of the present invention is the oral cavity image pickup apparatus, wherein said second holding means has a shape of larger width than width of said first holding means in a boundary portion with said second holding means.

A supplementary aspect of the present invention is the oral cavity image pickup apparatus, wherein said holding means forms a substantially key-hole shape all over said first holding means and said second holding means.

A still supplementary aspect of the present invention is the oral cavity image pickup apparatus, wherein said second holding means has a curved shape at a boundary portion between said first holding means and said second holding means with respect to said first holding means.

A still supplementary aspect of the present invention is the oral cavity image pickup apparatus, wherein said image pickup means continuously or intermittently rotates with a predetermined region of said holding means as a base point.

One aspect of the present invention is the oral cavity image pickup apparatus, further comprising image processing means of joining plural signals from said image pickup means together as one image.

Another aspect of the present invention is the oral cavity image pickup apparatus, further comprising display means capable of selectively displaying each of a signal from said image processing means and plural signals from said image pickup means.

Still another aspect of the present invention is the oral cavity image pickup apparatus, wherein said holding means is made of transparent material or material having permeability.

Yet another aspect of the present invention is the oral cavity image pickup apparatus,
wherein said holding means comprises:
driving means of driving said image pickup means;
power supply for supplying electric power to said image pickup means and said image pickup assisting means; and
radio signal output means of outputting a signal image-picked up by said image pickup means.

Still yet another aspect of the present invention is the oral cavity image pickup apparatus, wherein said image pickup means and said holding means are made integral with each other so as to enable them to be disassembled respectively.

A further aspect of the present invention is the oral cavity image pickup apparatus, wherein a shape of said holding means is a closed curve including at least two holding areas, in which said holding means is held, as a whole and wherein portions including at least two holding areas of said closed curve are on the same plane.

DESCRIPTION OF SYMBOLS

Figure 1:
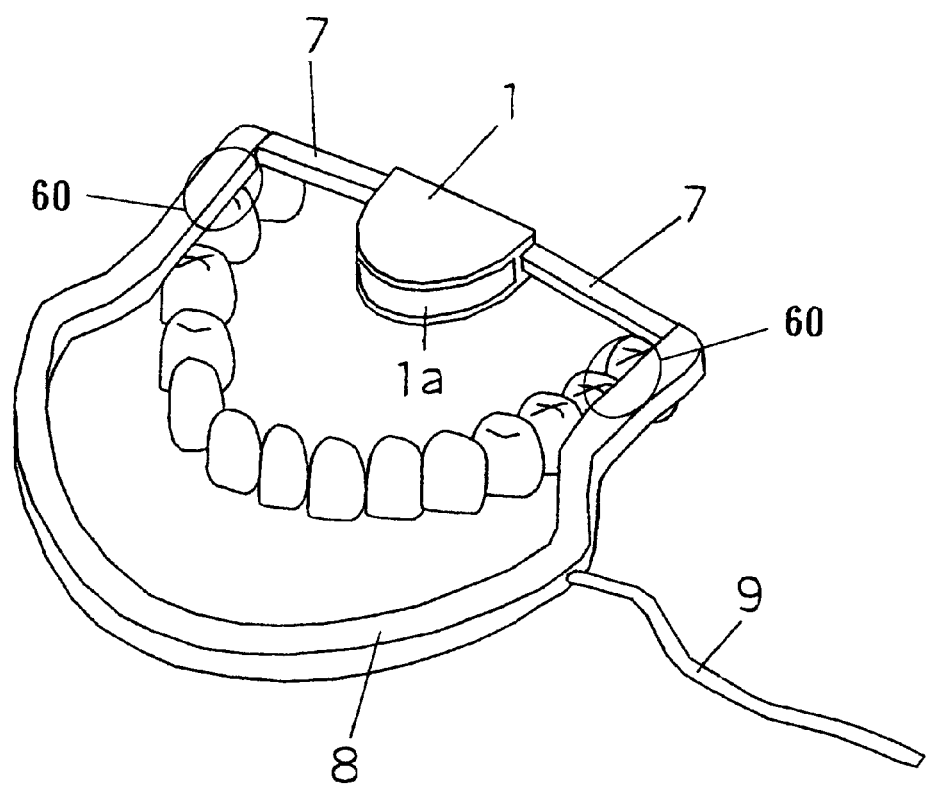
FIG. 1 is an external view showing an intra-oral cavity image pickup apparatus according to a first embodiment of the present invention.

1 Image pickup unit holder
2 Circuit substrate
3 Solid state imaging device
4 Fish-eye object lens
5 Image pickup system
6 White LEDs
7 Intra-oral cavity holding means
8 Wrong-insertion preventing guard
9 Cable cord
10 Molar
60 Bitten portion
1001 Opener for fitting
1002 Inside image pickup unit
1004 Outside image pickup unit
1005, 1011, 1013 Extra-oral cavity holding means
1012 Pickup holding means
1030 Bitten portion

PREFERRED EMBODIMENTS OF THE INVENTION

Hereinafter, with reference to FIGS. 1 to 23, the description will be made of embodiments according to the present invention. In this respect, in those drawings, portions having the same functions are designated by the identical reference numerals, and description repeated will be omitted.

(First Embodiment)

Figure 2:
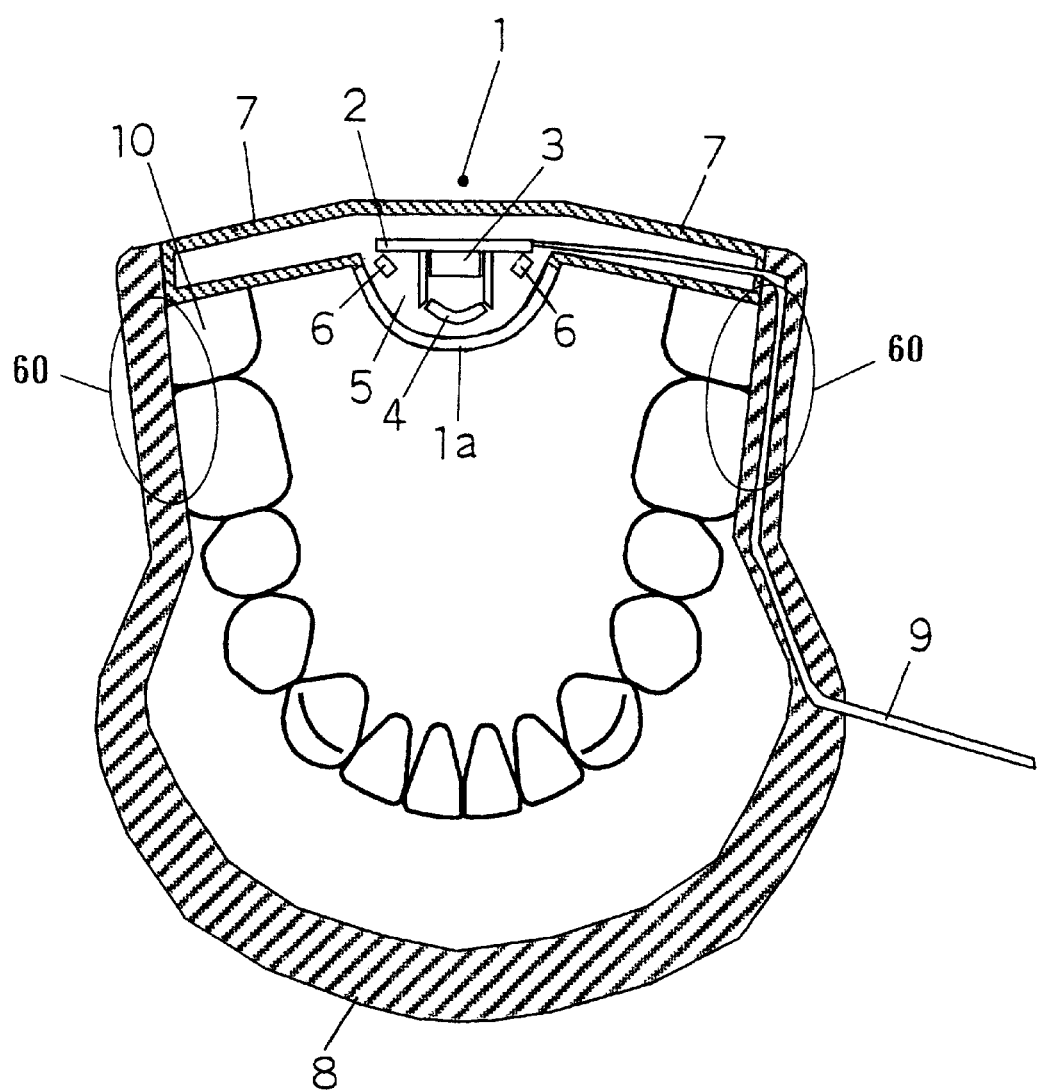
FIG. 2 is a partial cross sectional plan view showing the intra-oral cavity image pickup apparatus according to the first embodiment of the present invention.
Figure 3:
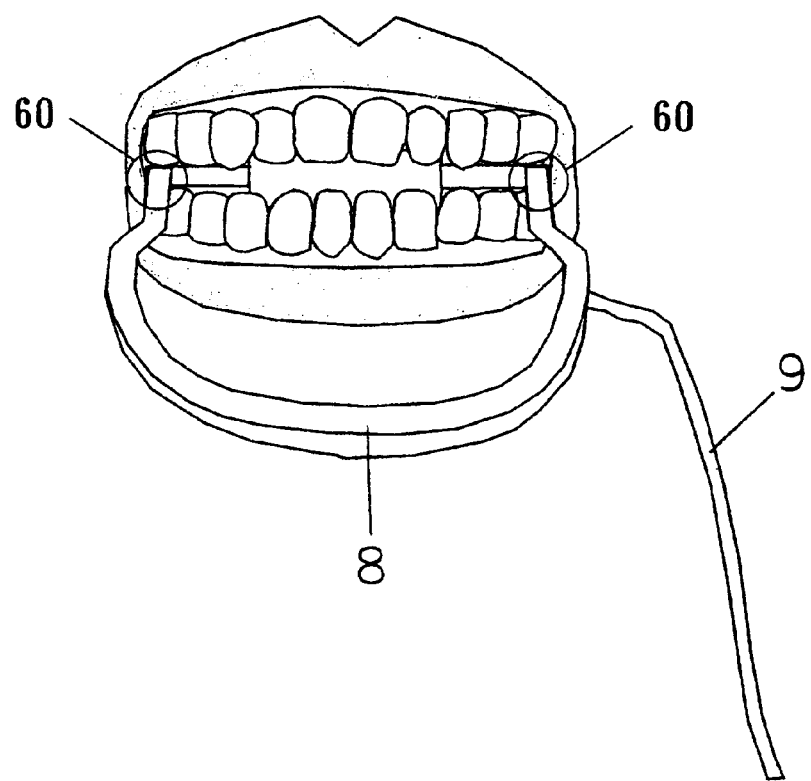
FIG. 3 is an use image front view showing the intra-oral cavity image pickup apparatus according to the first embodiment of the present invention.
Figure 4:
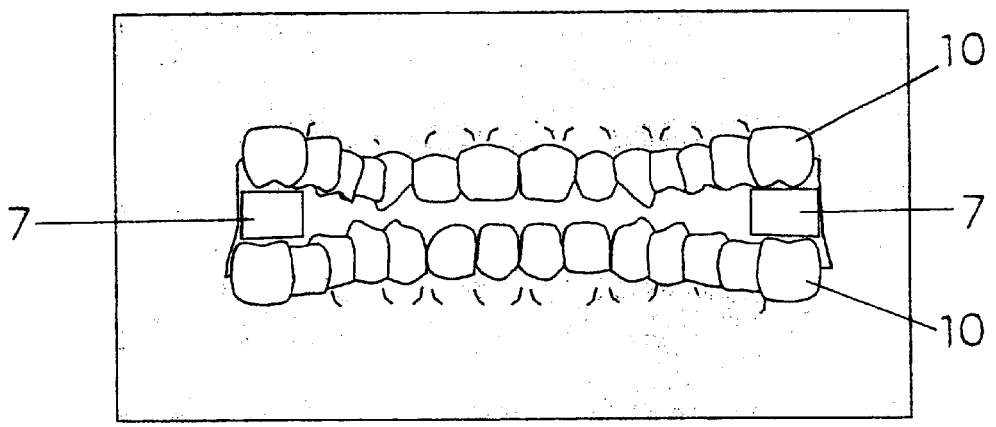
FIG. 4 is an image view for the interior of oral cavity obtained by picking up with the intra-oral cavity image pickup apparatus according to the first embodiment of the present invention.

FIG. 1 is an external view showing an intra-oral cavity image pickup apparatus according to a first embodiment of the present invention; FIG. 2 is a partial cross sectional plan view showing the intra-oral cavity image pickup apparatus; FIG. 3 is an use image front view showing the intra-oral cavity image pickup apparatus; and FIG. 4 is an image view showing an image for the interior of the oral cavity obtained by image-picking up with the intra-oral cavity image pickup apparatus. In this case, however, the "inside the oral cavity" means within space which spreads toward the throat with the upper and lower dentition a boundary, and the "outside the oral cavity" means the inside of the lips and a portion toward the exterior thereof with the upper and lower dentition a boundary. This definition applies to each embodiment hereinafter.

In FIGS. 1 and 2, reference numeral 1 denotes an image pickup unit holder to be inserted into the oral cavity, and the image pickup unit holder 1 has an incident window 1a for taking in image pickup light on a semi-elliptic circumferential surface, and window material made of glass capable of guiding light, transparent resin or the like is hermetically fixed to this incident window 1a. However, the entire circumference of the image pickup unit holder 1 may be made of transparent resin in place of the window material, whereby the number of parts can be reduced to simplify the assembly process.

Reference numeral 5 shown in FIG. 2 denotes an image pickup system provided with a solid state imaging device 3 such as CCD installed into a circuit substrate 2, and a fish-eye object lens 4, which is a super-wide angle lens having a visual field of about 180°. A plurality of white LEDs 6 for illumination are installed in the circuit substrate 2, and these white LEDs 6 corresponding to light projecting means of the present invention can be disposed around the image pickup system 5 to thereby enable the entire interior of the oral cavity to be uniformly irradiated. The image pickup system 5 and the white LEDs 6 are incorporated in the image pickup unit holder 1. However, the illumination by the projecting means of the present invention may not be incorporated in the image pickup unit holder 1, but the interior of the oral cavity may be irradiated from without the oral cavity as a separate configuration. In this respect, the fish-eye object lens 4 is provided with an iris diaphragm, but is omitted in this figure.

Reference numeral 7 denotes intra-oral cavity holding means of holding between the molar 10 and a milk molar, or between the upper and lower chins in the vicinity of the molar 10 or the milk molar. The intra-oral cavity holding means 7 is configured such that the image pickup unit holder 1 is integrally fixed. Reference numeral 8 denotes a wrong-insertion preventing guard for preventing the image pickup unit holder 1 and the intra-oral cavity holding means 7 from being erroneously swallowed or from being fallen into the throat, and is integrally fixed to the intra-oral cavity holding means 7.

This wrong-insertion preventing guard 8 has been manufactured such that a side to be disposed inside the oral cavity during use is made narrow, a side to be exposed outside the oral cavity is widened, and it is made into a shape of a key-hole whose bottom has been rounded, and therefore, it is easy to hold it in hand, and it spreads wider than the oral cavity half way. Therefore, this widened portion serves as a stopper, and prevents it from being erroneously inserted to the depths of the throat excessively, not injuring the throat. Also, even though it is erroneously inserted into the oral cavity by holding the image pickup unit holder 1, it will not enter the oral cavity because the outside of the oral cavity has been made wide, and therefore, any mounting error does not occur. In this respect, the shape of this wrong-insertion preventing guard 8 may be made into a substantially U-character shape in as-is width from the oral cavity side, and may be bent without the oral cavity to be used as a stopper.

A cable cord 9 for transmitting a video output signal, a driving signal or the like from the circuit substrate 2 is inserted into the intra-oral cavity holding means 7, and is taken out from the end portion or the wrong-insertion preventing guard 8. The cable cord 9 taken out is connected to the power supply, the external camera circuit, the monitor TV or the like, although not shown.

An operation of the intra-oral cavity image pickup apparatus according to the present embodiment having the above described configuration is as follows. The wrong-insertion preventing guard 8 is held in hand, and is mounted into the oral cavity in such a manner that the intra-oral cavity holding means 7 and bitten portions 60, which are a portion of the wrong-insertion preventing guard 8, are bitten between the molar portions as shown in FIG. 3. When the wrong-insertion preventing guard 8 is mounted, the image pickup unit holder 1 is inserted into the oral cavity, and is held in the depths of the oral cavity with stability. Thereby, it is possible to observe the other side of the teeth, the tongue side, and the gums on the palate side from the inside of the oral cavity through the use of the image pickup system 5. At this time, the fish-eye object lens 4 is a wide angle lens having a visual field of 180° in the image pickup system 5, and it becomes possible to observe the entire dentition within the oral cavity with one lens at the same time.

Since the bitten portions 60 are adapted to bite portions of the molar 10 as shown in FIGS. 1 to 3, when an image projected on the monitor TV is viewed as shown in FIG. 4, such obstacles as to hinder visual recognition can be reduced from the image pickup visual field. Also, since the intra-oral cavity holding means 7 is sandwiched therebetween, the user goes into a state in which the oral cavity has been slightly opened, and it is possible to image-pick up and observe the upper and lower dentition without the upper and lower teeth or occlusion of chins being overlapped. Also, in a state in which the intra-oral cavity holding means 7 is held by a bite of the upper and lower teeth, the image pickup unit holder 1 is adapted to position near midway between upper and lower teeth at all times, and does not become impartial on either of the upper and lower teeth, and therefore, it is not necessary to make any special positioning for image picking up.

As described above, according to an intra-oral cavity image pickup apparatus of the present embodiment, a row of teeth as viewed from the back, which is the inside of the oral cavity, a state of teeth, and a state of gums within the oral cavity can be obtained instantaneously as one image for the entire mouth.

Also, since an image of the entire dentition can be instantaneously obtained, time can be shortened when the content of an individual's observation is recorded for preservation.

(Second Embodiment)

Figure 5:
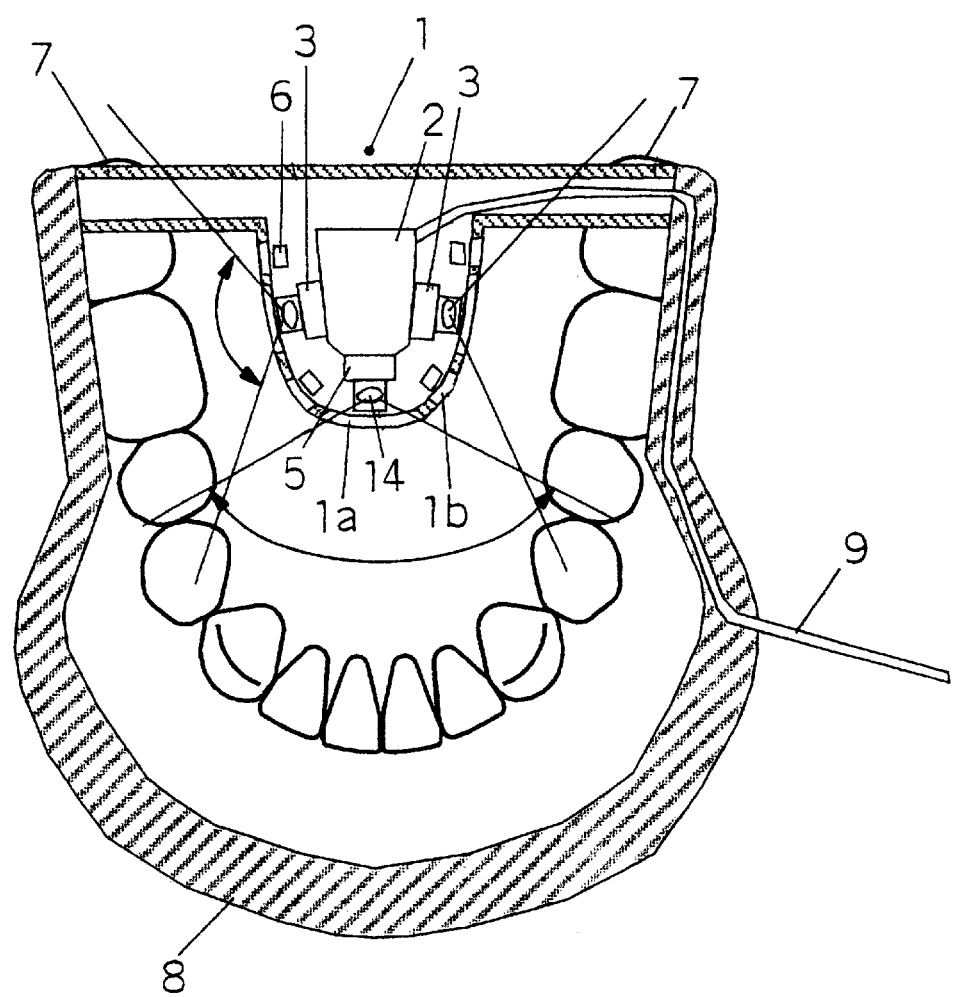
FIG. 5 is a partial cross sectional plan view showing the intra-oral cavity image pickup apparatus according to a second embodiment of the present invention.
Figure 6:
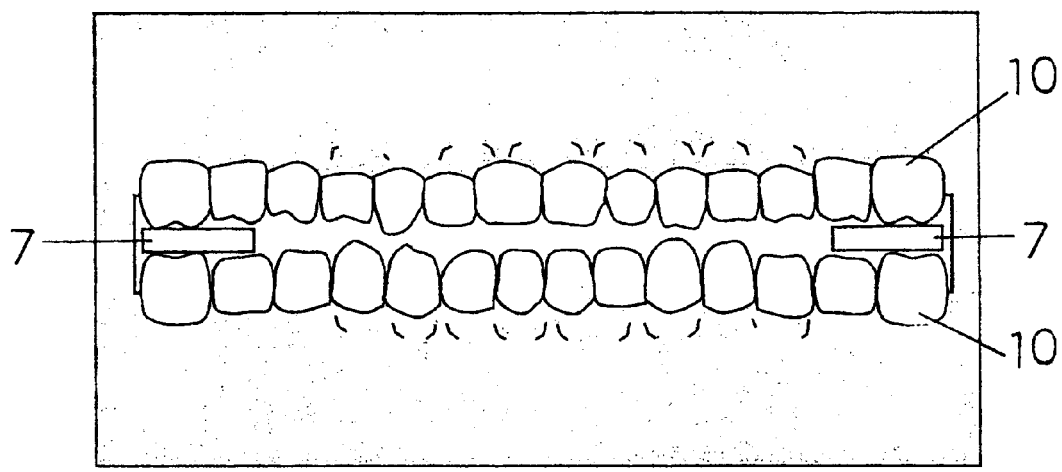
FIG. 6 is an image view for the interior of oral cavity obtained by picking up with the intra-oral cavity image pickup apparatus according to the second embodiment of the present invention.

FIG. 5 is a partial cross sectional plan view showing an intra-oral cavity image pickup apparatus according to a second embodiment of the present invention, and FIG. 6 is an image view showing an image for the interior of the oral cavity obtained by image-picking up through the use of the intra-oral cavity image pickup apparatus.

In FIG. 5, reference numeral 1 denotes an image pickup unit holder to be inserted into the oral cavity, and the image pickup unit holder 1 has an incident window 1a for taking in image pickup light on a semi-elliptic circumferential surface, and a light throwing unit 1b for illumination. Window material such as glass capable of guiding light or transparent resin is hermetically fixed to the incident window 1a and the light throwing unit 1b. An image pickup system 5 having three each of solid state imaging devices 3 such as CCD and object lenses 14 therein, and a plurality of white LEDs 6 for illumination are disposed so as to irradiate the entire interior of the oral cavity, and are incorporated in the circuit substrate 2. In this respect, the object lens 14 is provided with an iris diaphragm, but is omitted in this figure.

Reference numeral 7 denotes intra-oral cavity holding means to which the image pickup unit holder 1 has been fixed; and 8, a wrong-insertion preventing guard.

In the image pickup system 5, the solid state imaging device 3 and the object lens 4 have such a range of angle of view (indicated by an arrow in the drawing) as to allow a plurality of teeth to be photographed respectively. The range of angle of view has been set to, for example, a horizontal angle of view of about 120°, and the solid state imaging device 3 and the object lens 14 which constitute the image pickup system 5 are disposed in a substantially U-character shape within the image pickup unit holder 1 so as to image-pick up each group of a plurality of teeth substantially from the front.

According to the intra-oral cavity image pickup apparatus of the present embodiment having such a configuration, an image is taken in from the image pickup system 5 having a plurality of solid state imaging devices 3, whereby each group of a plurality of teeth constituting the dentition is to be image-picked up from substantially the front, and the entire dentition can be observed everywhere without adjacent teeth being overlapped, and with the exception of portions to be hidden behind the adjacent teeth or which constitute a dead angle.

Figure 10:
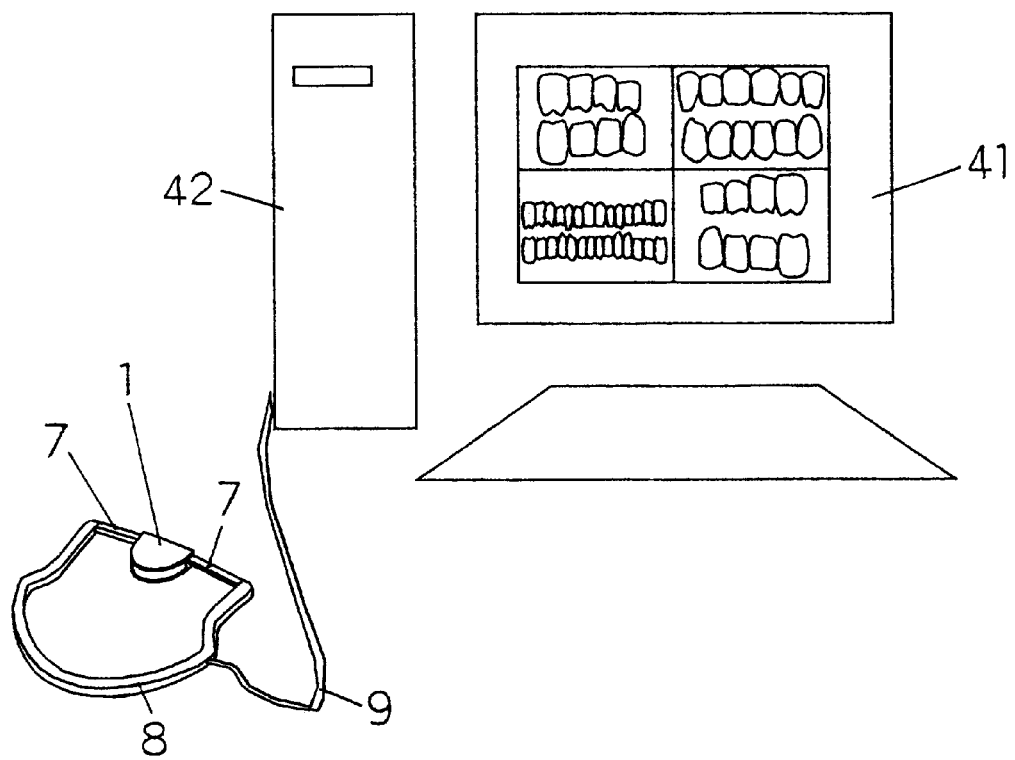
FIG. 10 is a system view showing the intra-oral cavity image pickup apparatus according to the second embodiment of the present invention.

Image information from the image pickup system 5 is taken in an image processing circuit mounted onto, for example, the circuit substrate 2 or an external camera circuit, and is subjected to a treatment for joining plural image information together, whereby such a panoramic image as shown in FIG. 6 can be obtained. FIG. 10 shows a system configured by an intra-oral cavity image pickup apparatus according to the present embodiment and its surrounding equipment for obtaining the panoramic image. This system is provided with a display unit 41 for selectively displaying images obtained by joining plural image signals from the image pickup system 5 together into one, and respective images of signals from the image pickup system 5, and the system can be switched to screen divided display in which the screen is divided and these images are displayed.

The system has image storage means 42 of storing images, and image data can be simply pigenholed.

In this respect, in the present embodiment, the description has been made of a case where the image pickup system 5 has three each of the solid state imaging devices 3 and the object lenses 14, but for the object lens 14, a lens having a narrow range of angle of view may used and numbers of the imaging devices and the object lenses which constitute the image pickup system 5 may be increased. Further, for some of the object lenses 14, a fish-eye lens having a wide range of angle of view may be used and numbers of the imaging devices and the object lenses which constitute the image pickup system 5 may be reduced.

As regards the treatment of the image processing circuit, every one image may be successively displayed as respectively independent image information from each image pickup system 5, and plural images may be arranged side by side for display on the screen.

(Third Embodiment)

Figure 7:
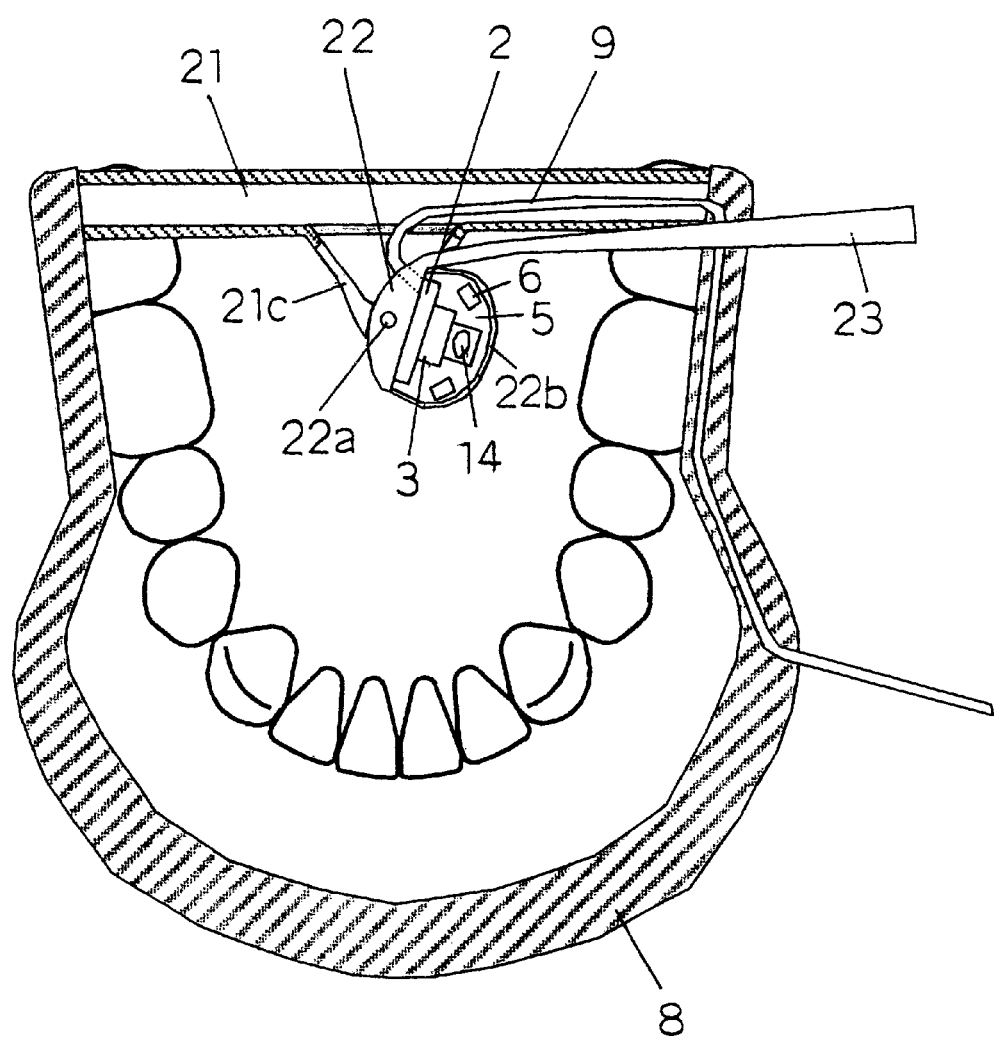
FIG. 7 is a partial cross sectional plan view showing the intra-oral cavity image pickup apparatus according to a third embodiment of the present invention.

FIG. 7 is a partial cross sectional plan view showing an intra-oral cavity image pickup apparatus according to a third embodiment of the present invention, and in FIG. 7, reference numeral 21 denotes intra-oral cavity holding means to be inserted into the oral cavity, and the intra-oral cavity holding means 21 has a semicircular receiver and an opening 21c.

Reference numeral 22 denotes an image pickup unit holder mounted to this intra-oral cavity holding means 21, and the image pickup unit holder 22 is adapted to be able to rotate along the lip with a rotatable shaft 22a as a base point. An image pickup system 5 having a solid state imaging device 3 such as CCD installed in the circuit substrate 2 and an object lens 14, and a white LED 6 for illumination are mounted onto this image pickup unit holder 22, and window material made of glass capable of guiding light, transparent resin or the like is hermetically fixed to an incident window 22b. However, as in other embodiments, the entire image pickup unit holder 22 may be made of transparent material instead of the window material.

A cable cord 9 for transmitting a video output signal, a driving signal or the like from the circuit substrate 2 is inserted into the intra-oral cavity holding means 21 through the opening 21c, and is hermetically sealed with elastic material such as rubber, and is taken out from the end portion through the guard 8.

An operation of the intra-oral cavity image pickup apparatus according to the present third embodiment having the above described configuration is as follows. That is, by manipulating a protruding piece 23 which is exposed to the outside from the oral cavity in the image pickup unit holder 22 shown in FIG. 7, the back side and gums of the teeth on the inside of the oral cavity are observed and image-picked up while rotating the image pickup unit holder 22. As regards this operation, images may be successively picked up while the image pickup unit holder 22 is being rotated, and may be stepwise fixed for taking in the images for observation.

As in the second embodiment, successively observed continuous images are subjected to a treatment for joining plural image information together through the use of the image processing circuit mounted onto the circuit substrate 2 or the external camera circuit, and may be reproduced as such a panoramic image as shown in FIG. 6. Also, image information may be taken in as static image for each predetermined angle while being successively observed continuously, and may be subjected to a treatment for joining plural image information together through the use of the image processing circuit similarly to be reproduced as a panoramic image.

Also, every one image may be displayed as independent image information respectively, and plural images may be arranged and displayed side by side.

According to an intra-oral cavity image pickup apparatus of the present embodiment as described, an image is taken in by rotating the image pickup system 5, whereby each group of a plurality of teeth is to be image-picked up from substantially the front, and the entire dentition can be observed everywhere without adjacent teeth being overlapped, and with the exception of portions to be hidden behind the adjacent teeth or which constitute a dead angle.

In this respect, in the present embodiment, any angle of view of the object lens 14 may be taken as long as it is within a range of 30° to 120°, and an angle of rotation, which is a position in the image pickup system 5, at which an image is taken in, is determined by the angle of view. In some cases, a fish-eye lens having a larger angle of view may be used for the object lens, and in this case, the angle of rotation becomes smaller.

As regards the means of rotation, the description has been made of a case where, for example, a protruding piece 23 of the image pickup unit holder 22 provided so as to be exposed outside the oral cavity is manually moved to thereby rotate the image pickup system, and the image pickup system is once stopped every a certain angle of rotation to take an image in, but the present invention is not limited thereto, and the structure may be arranged such that an image is taken in every a certain angle of rotation by driving using, for example, a super-small size motor or the like.

As regards illumination, the white LED 6 may be fixed on the slide base 21 side.

(Fourth Embodiment)

Figure 8:
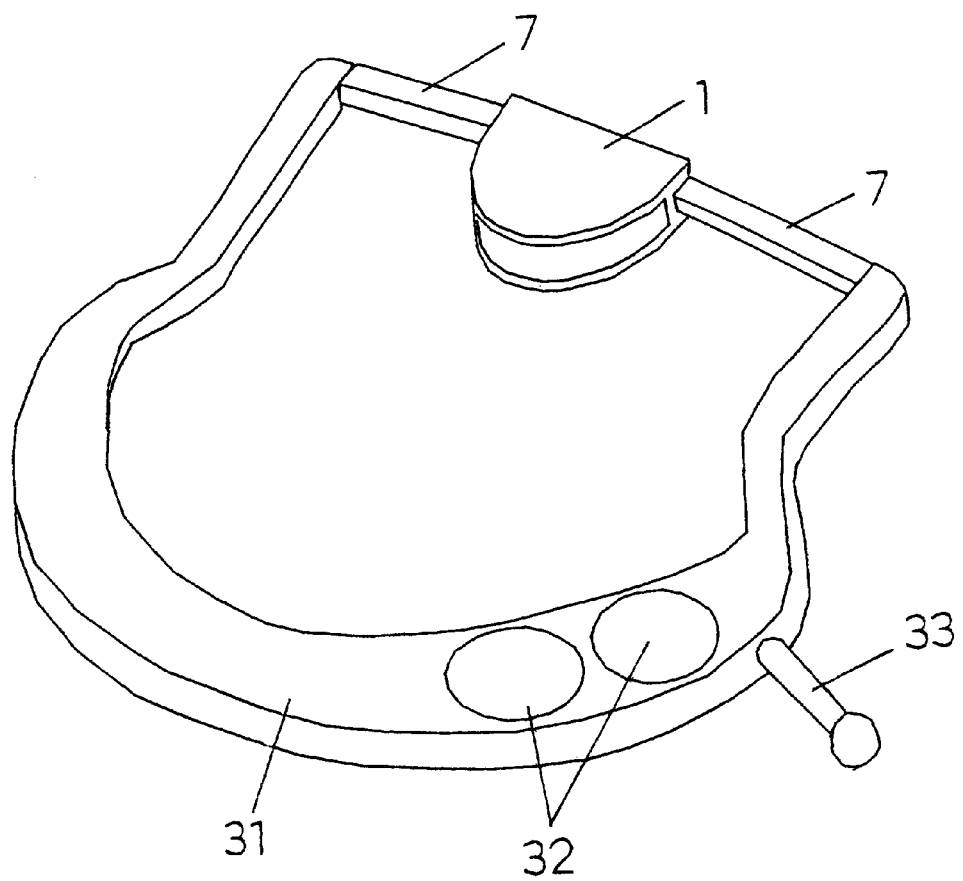
FIG. 8 is an external view showing an intra-oral cavity image pickup apparatus according to a fourth embodiment of the present invention.

FIG. 8 is an external view showing an intra-oral cavity image pickup apparatus according to a fourth embodiment of the present invention, and in FIG. 8, reference numeral 1 denotes an image pickup unit holder to be inserted into the oral cavity. An image pickup system 5 having a solid state imaging device 3 such as CCD and an object lens 14 therein, and a plurality of white LEDs 6 for illustration are disposed so as to irradiate the entire interior of the oral cavity, and are incorporated in a circuit substrate 2.

Reference numeral 7 denotes an intra-oral cavity holding means to which the image pickup unit holder 1 has been fixed; and 31, a wrong-insertion preventing guard. To the circuit substrate 2 or this wrong-insertion preventing guard 31, a miniaturized camera circuit, and an image processing circuit are installed therein, and a battery 32 as power supply is mounted so as to enable it to be replaced. Reference numeral 33 denotes a radio wave signal transmitter.

According to the intra-oral cavity image pickup apparatus of the present embodiment having such a configuration, it becomes possible to make it cordless by combining with a monitor TV (not shown), onto which a receiver has been mounted, for use.

In this respect, the present embodiment has been a combination with the first embodiment, but it may be possible to combine with the second or third embodiment, further a fifth embodiment to be described later.

(Fifth Embodiment)

An intra-oral cavity image pickup apparatus according to a fifth embodiment of the present invention has the same basic operations as each of the above described embodiments, but is configured such that each component member is made integral with one another so as to enable it to be disassembled.

Figure 9:
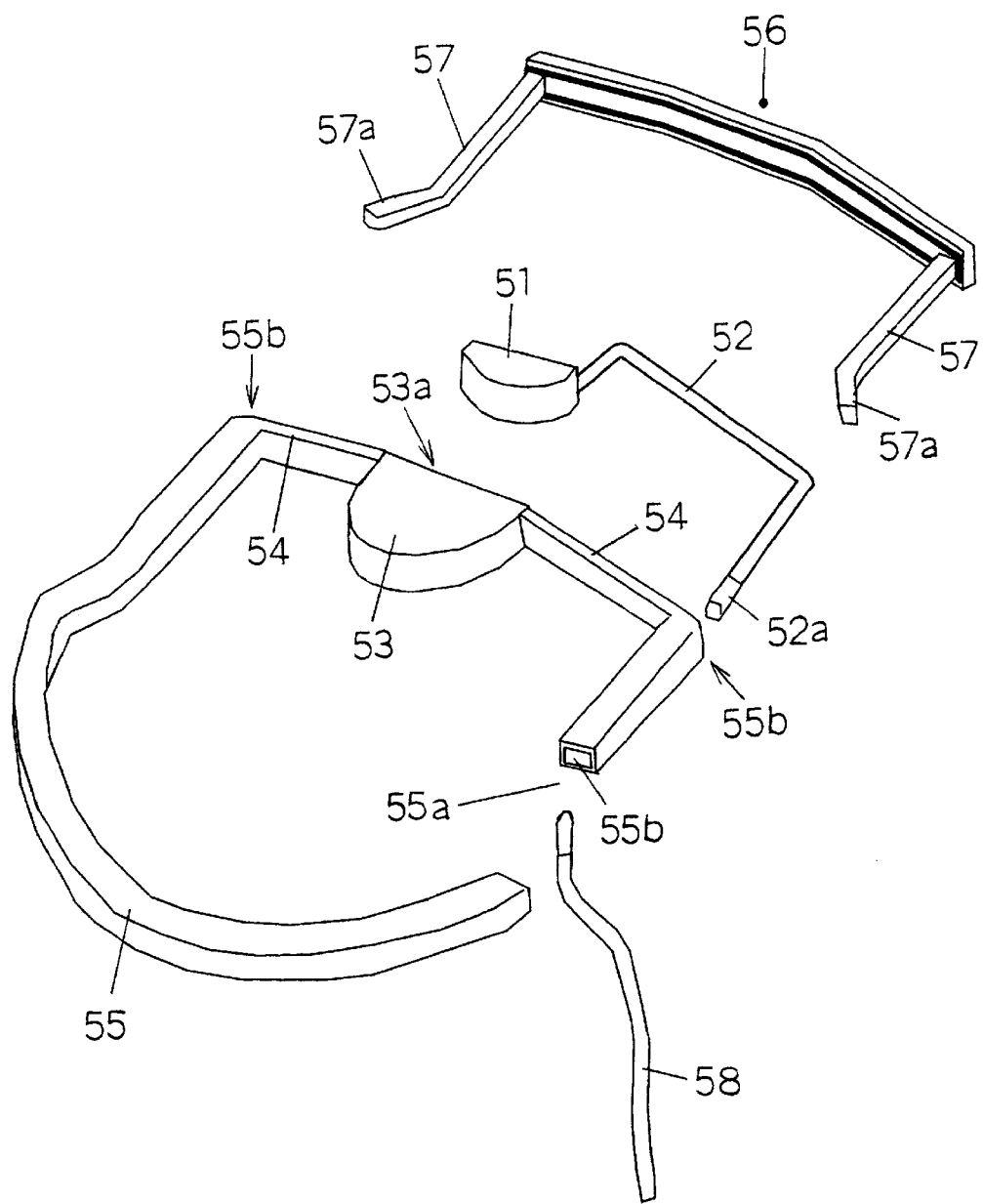
FIG. 9 is an external view showing an intra-oral cavity image pickup apparatus according to a fifth embodiment of the present invention.

FIG. 9 is an external view showing an intra-oral cavity image pickup apparatus according to a fifth embodiment of the present invention, and in FIG. 9, reference numeral 51 denotes an image pickup unit body in which an image pickup system 5 having a solid state imaging device 3 and an object lens 14, and white LEDs 6 for illumination are disposed to irradiate the entire interior of the oral cavity and are installed in a circuit substrate 2. The image pickup unit body 51 is hermetically covered with transparent resin or the like, and an electric connecting leg 52 with a connector 52a at its tip end is mounted to the end portion. However, the image pickup unit body 51 may be one image pickup system 5 using the fish-eye object lens 4 shown in the first embodiment, or a plurality of image pickup systems 5 shown in the second embodiment.

Reference numeral 53 denotes an image pickup unit holder having an opening 53a, and an intra-oral cavity holding means 54 for holding in the mouth, and a wrong-insertion preventing guard 55 are integrally molded using transparent resin. This wrong-insertion preventing guard 55 has a cut-out portion 55a in a portion located without the oral cavity, and a detachable hole 55b at the side of the intra-oral cavity holding means 54, and this detachable hole 55b passes through the cut-out portion 55a.

Reference numeral 56 denotes a holder lid for covering the image pickup unit holder 53 and the intra-oral cavity holding means 54, and in order to hermetically cover, an elastic body such as rubber is fixed within, or a protrusion is integrally formed. A mounting arm 57 to be inserted into the detachable hole 55b in the wrong-insertion preventing guard 55 is integrally provided on the holder lid 56, and the mounting arm 57 is provided with a stopper portion 57a to be used for fixing after the insertion.

Reference numeral 58 denotes a connecting cable, which is means of connecting to power supply, an external camera circuit, a monitor TV or the like, which are not shown.

An operation of the intra-oral cavity image pickup apparatus according to the present embodiment having the above described configuration is as follows. That is, the image pickup unit body 51 is inserted into the image pickup unit holder 53, an electric connecting leg 52 is caused to project from the cut-out portion 55a in the wrong-insertion preventing guard 55, thereafter the mounting arm 57 of the holder lid 56 is mounted to the detachable hole 55b, the mounting arm 57 is inserted until the stopper portion 57a is restrained by the wrong-insertion preventing guard 55 for fixing, whereby the image pickup unit body 51 is hermeticallly covered and the connecting cable 58 is connected to the connector 52a.

The above described operation causes the intra-oral cavity image pickup apparatus according to the present embodiment to be ready for the use, and by inserting it into the oral cavity in the same manner as each of the embodiments, it becomes possible to image-pick up and observe the other side of the teeth, the tongue side, and the gums on the palate side from within the oral cavity.

There is no possibility that the holder lid 56 comes off during use because the mounting arm 57 is provided with a stopper portion 57a, and the image pickup unit body 51 does not come off. Also, the mounting arm 57 is long and has elasticity at the tip end portion, and can be removed by strongly drawing it out.

As described above, according to the intra-oral cavity image pickup apparatus of the present embodiment, the image pickup unit body 51 can be detachably mounted, and therefore, becomes replaceable, and a plurality each of the image pickup unit holders 53, which cover the outside, the intra-oral cavity holding means 54, and the wrong-insertion preventing covers 55 and the holder lids 56 are prepared, whereby the frequency in sterilization can be reduced.

The image pickup unit holder 53 for covering the outside, the intra-oral cavity holding means 54, the wrong-insertion preventing cover 55, and the holder lid 56 can be molded using transparent resin, can be mass-produced, and can be used as a disposable member, or can be hygienically used by keeping in large quantities, and troubleness of sterilization when a large number of people are observed like dental examination can be eliminated.

The image pickup unit holder 53, the intra-oral cavity holding means 54, the wrong-insertion preventing cover 55, and the holder lid 56 are prepared in various sizes, whereby correspondence to infants to adults can be easily performed.

(Sixth Embodiment)

Figure 11:
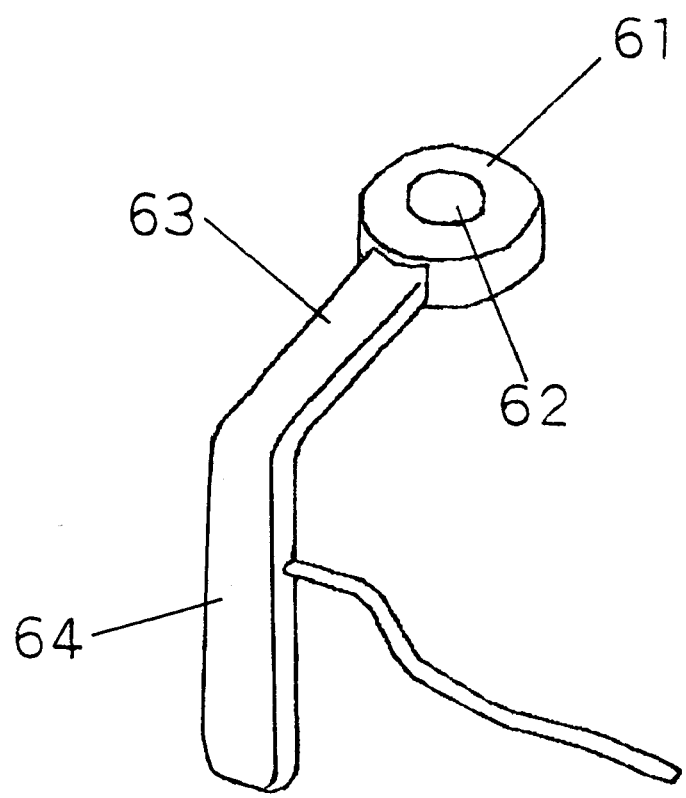
FIG. 11 is an external view showing an intra-oral cavity image pickup apparatus according to a sixth embodiment of the present invention.
Figure 12:
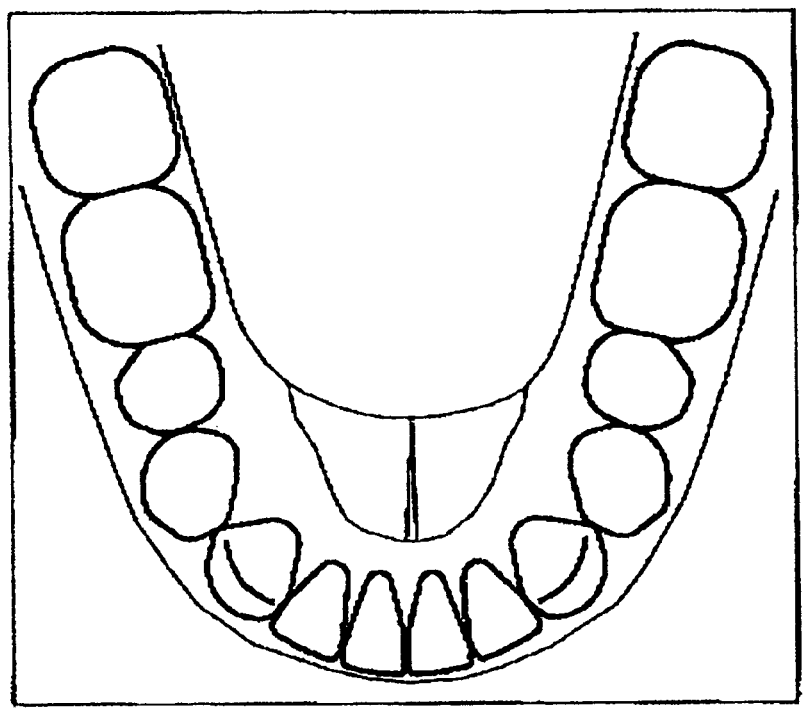
FIG. 12 is an image view for the interior of the oral cavity obtained by picking up with the intra-oral cavity image pickup apparatus according to the sixth embodiment of the present invention.

FIG. 11 is an external view showing an intra-oral cavity image pickup apparatus according to a sixth embodiment of the present invention, and FIG. 12 is an image view showing an image for the interior of oral cavity obtained by image-picking up by an intra-oral cavity image pickup apparatus according to the present embodiment.

In FIG. 11, reference numeral 61 denotes an image pickup unit holder to be inserted into the oral cavity, and the image pickup unit holder 61 has an incident window 62 for taking in image pickup light and projecting light on the top surface thereof, and window material such as glass capable of guiding light or transparent resin is hermetically fixed, and an image pickup system having a solid state imaging device such as CCD and an object lens therein and for example, white LED for illumination are positioned so as to irradiate the entire interior of the oral cavity, and are incorporated in the circuit substrate.

Also, on the under surface of the image pickup unit holder 61, the incident window and the image pickup system are similarly incorporated.

Reference numeral 63 denotes intra-oral cavity holding means, onto which the image pickup unit holder 61 has been fixed; and 64, a wrong-insertion preventing guard.

An operation of the intra-oral cavity image pickup apparatus according to the present embodiment having the above described configuration is as follows. That is, when the intra-oral cavity image pickup apparatus according to the present embodiment is inserted into the mouth until the wrong-insertion preventing guard 64 abuts upon the chin for picking up an image, a collective image for the interior of the oral cavity which belongs to the upper and lower chin portions can be obtained. FIG. 12 shows an example of a collective image for the tongue side within the oral cavity which belongs to the lower chin, obtained by image-picking up from the under surface.

As described above, according to the intra-oral cavity image pickup apparatus of the present embodiment, an independent, arch-shaped collective image can be obtained for dentition of each of the upper and lower chin portions. Such an arch-shaped collective image gives information on disorder of dentition, which becomes effective data in the medical examination.

In this respect, in the present embodiment, the description has been made of a case where each of the incident window and the image pickup system are provided on both sides of the image pickup unit holder 61, but only a single side will suffice, and in that case, the top and bottom are inverted to be utilized, whereby a collective image for the interior of the oral cavity of both the upper and lower chin portions can be obtained.

(Seventh Embodiment)

Figure 13:
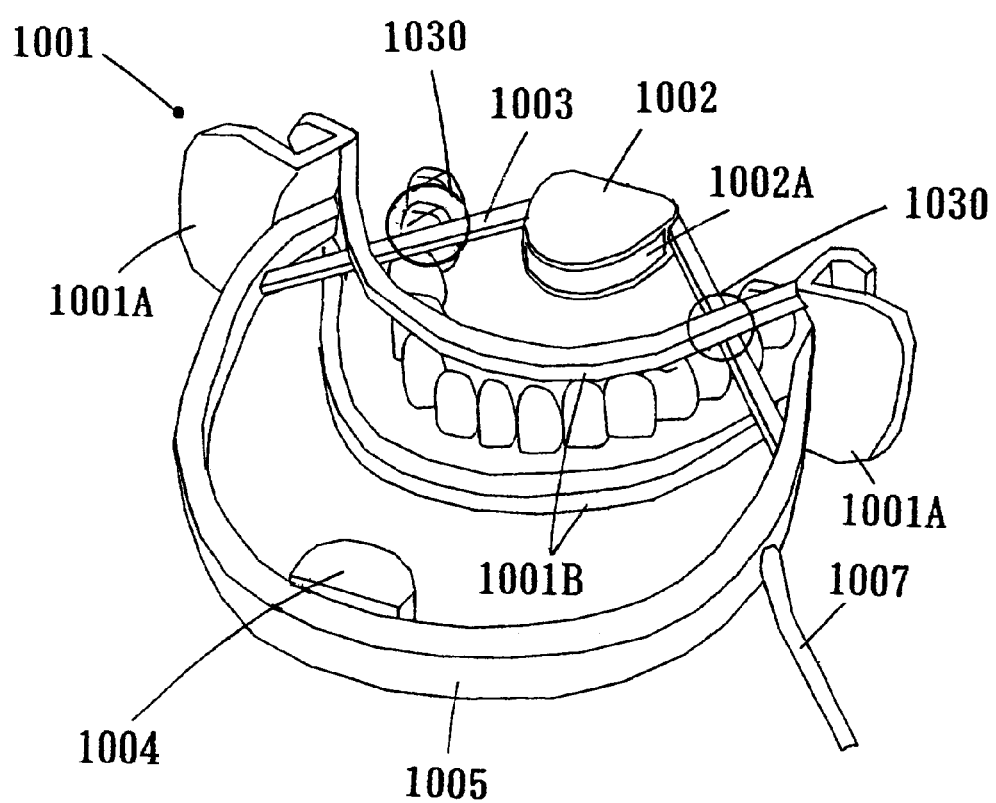
FIG. 13 is an external view showing an oral cavity pickup apparatus according to a seventh embodiment of the present invention.
Figure 14:
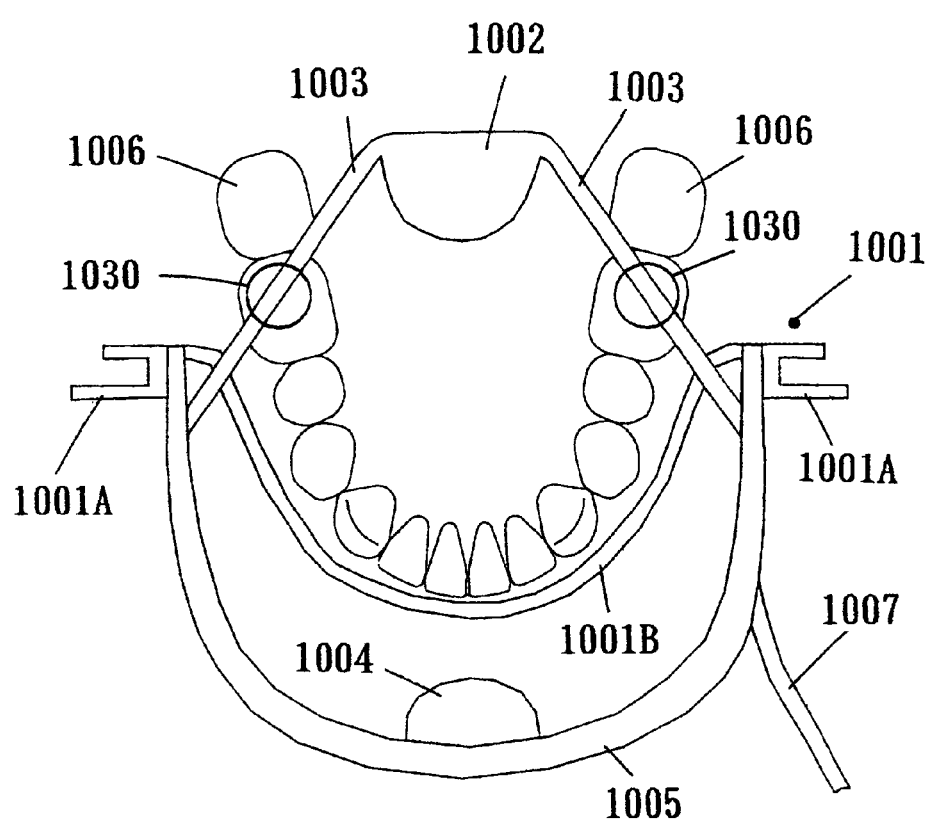
FIG. 14 is a partial cross sectional plan view showing the oral cavity pickup apparatus according to the seventh embodiment of the present invention.
Figure 15:
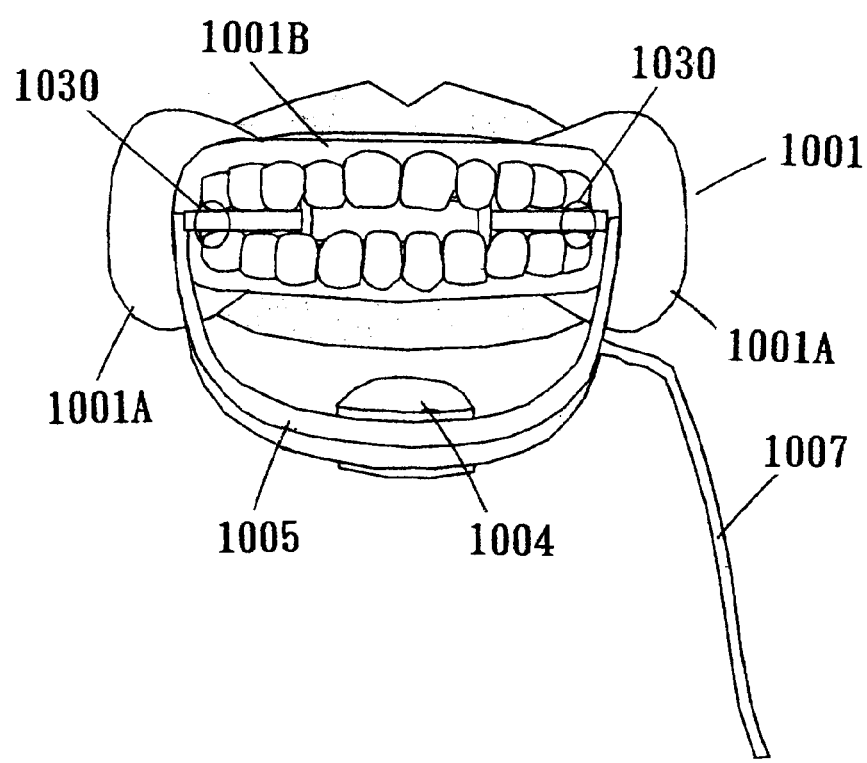
FIG. 15 is an use image front view showing the oral cavity pickup apparatus according to the seventh embodiment of the present invention.
Figure 16:
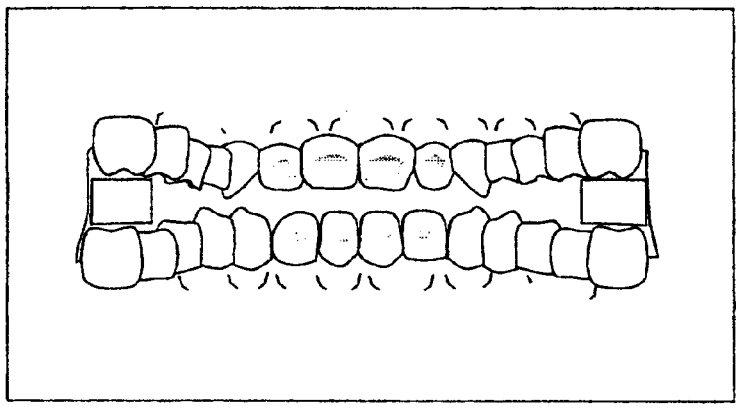
FIG. 16A is an image view for the interior of the oral cavity obtained by picking up with the oral cavity pickup apparatus according to the seventh embodiment of the present invention.
FIG. 16B is an image view for the interior of the oral cavity obtained by picking up with the oral cavity pickup apparatus according to the seventh embodiment of the present invention.
Figure 16:
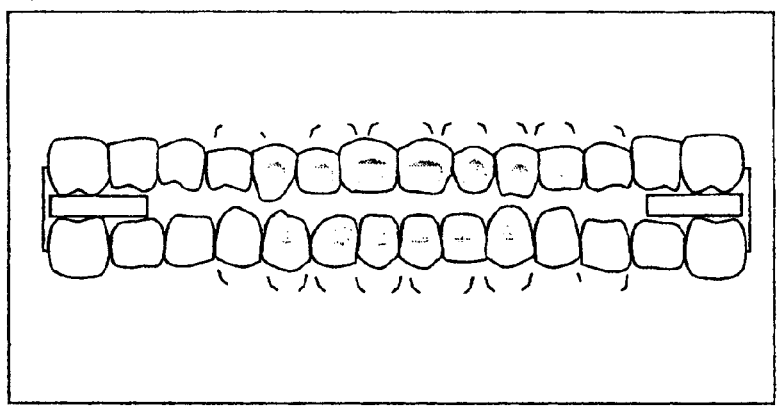
Figure 17:
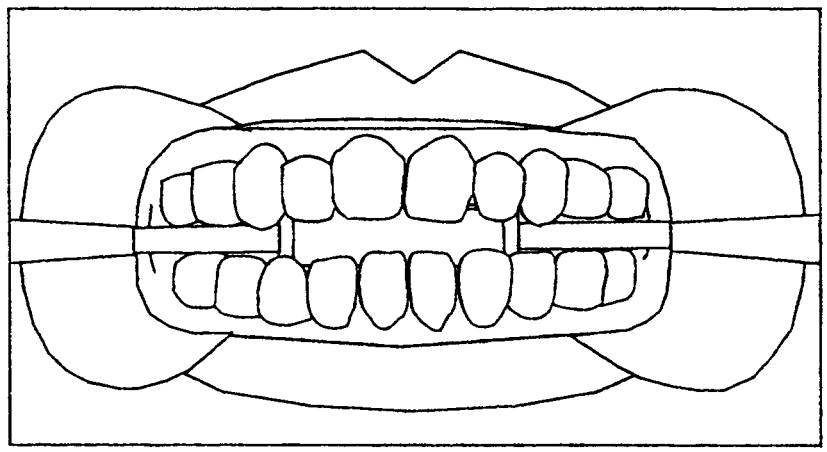
FIG. 17 is an image view for the exterior of the oral cavity obtained by picking up with the oral cavity pickup apparatus according to the seventh embodiment of the present invention.

FIG. 13 is an external view showing an oral cavity image pickup apparatus according to the seventh embodiment of the present invention; FIG. 14 is a partial cross sectional plan view showing the oral cavity image pickup apparatus; FIG. 15 is an use image front view showing the oral cavity image pickup apparatus; FIG. 16 is an image view showing an image for the interior of the oral cavity obtained by image-picking up by the oral cavity image pickup apparatus; and FIG. 17 is an image view showing an image for the exterior of the oral cavity obtained by image-picking up by the oral cavity image pickup apparatus.

In FIGS. 13 to 15, reference numeral 1001 denotes an opener for fitting into a lip right and left angle to fix the opened state, the opener has a lip receiver 1001A having a substantially quasi-horse shoe shaped cross section each on both sides, and two arch-shaped coupling arms 1001B for coupling these right and left lip receivers 1001A are provided for the upper gum and the lower gum. As regards the coupling arm 1001B, however, one coupling arm for, for example, the upper gum side will suffice. The height of the right and left lip receivers 1001A is length in which the lip receivers 1001A can be held in a state in which the mouth is opened when mounted in the oral cavity.

Reference numeral 1002 denotes an inside image pickup unit to be inserted into the oral cavity. This inside image pickup unit 1002 has an incident window 1002A for taking image pickup light in on the semi-elliptic circumferential surface, and there are incorporated a circuit substrate, a solid state imaging device such as CCD, a super-wide angle object lens, and white LED corresponding to light projecting means of the present invention as a light source for illumination therein although not shown.

Reference numeral 1003 denotes intra-oral cavity holding means of holding between a molar 1006 and a milk molar, or between the upper and lower chin in the vicinity of the molar 1006 and the milk molar, and the inside image pickup unit 1002 is integrally fixed.

Reference numeral 1004 denotes an outside image pickup unit. This outside image pickup unit 1004 has an incident window for taking image pickup light in on the semi-elliptic circumferential surface in the same manner as the inside image pickup unit 1002, and there are incorporated a circuit substrate, a solid state imaging device such as CCD, a super-wide angle object lens, and white LED corresponding to light projecting means of the present invention as a light source for illumination therein although not shown. In this respect, the light source for illumination of the outside image pickup unit 1004 may be omitted because external light such as indoor light can be utilized.

Reference numeral 1005 denotes extra-oral cavity holding means of fixing this outside image pickup unit 1004, and this extra-oral cavity holding means is fixed near the right and left lip receivers 1001A of the opener 1001. The other end of the intra-oral cavity holding means 1003 passes through between the upper and lower coupling arms 1001B of the opener 1001 and is fixed to the extra-oral cavity holding means 1005.

A cable cord 1007 for transmitting a video output signal, a driving signal or the like from the circuit substrate has been inserted into the extra-oral cavity holding means 1005 and the intra-oral cavity holding means 1003, and is taken out from the extra-oral cavity holding means 1005. The cable cord 1007 taken out is connected to the power supply, the external camera circuit, the monitor TV or the like, which are not shown.

An operation of the intra-oral cavity image pickup apparatus according to the present embodiment having the above described configuration is as follows. The right and left lip receivers 1001A of the opener 1001 are mounted into the oral cavity in such a manner that a bitten portion 1030, which is a portion of the intra-oral cavity holding means 1003, is bitten between the molar portions in FIG. 15 as shown in the figure. When the opener 1001 is mounted, the inside image pickup unit 1002 is inserted into the oral cavity, and is held in the depths of the oral cavity with stability. Thereby, it is possible to observe the other side of the teeth, the tongue side, and the gums on the palate side from the inside of the oral cavity as shown in FIG. 16A, and it is possible to observe the surface side of the teeth, and the gums on the lip side as shown in FIG. 17 at the same time through the use of the outside image pickup unit 1004 outside the oral cavity.

Also, the outside image pickup unit 1004 is movably mounted to the extra-oral cavity holding means 1005 although not shown, and it may be possible to successively observe the outside teeth and gum within the oral cavity while the outside image pickup unit being rotated along the extra-oral cavity holding means 1005.

The inside image pickup unit 1002 may be configured such that a plurality of CCDs are disposed within in such a manner that the dentition is divided and each group of a plurality of teeth faces the front, plural image information from these CCDs are joined together through the use of an image processing circuit mounted onto the circuit substrate or the external camera circuit, and if so, the observation can be made without portions to be hidden behind the adjacent teeth as shown in FIG. 16B.

Also, image information from the inside image pickup unit 1002 and the outside image pickup unit 1004 maybe independently displayed on the monitor TV screen respectively, and selective display which can be switched to the screen divided display, in which the screen is divided so as to be able to display these images at the same time, may be adopted. Also, if the system is provided with image storage means of storing images or image printing means, the image data will be able to be easily pigeonholed.

As described above, according to the present embodiment, a row of teeth, a state of teeth, and a state of gums within the oral cavity as viewed from the back, which is the inside of the oral cavity, can be obtained instantaneously as one image for the entire mouth, and the row of teeth, the state of teeth, and the state of gums as viewed from the front can be obtained instantaneously at the same time, and therefore, when the content of an individual's observation is recorded and preserved, and when data is pigeonholed, time can be shortened.

(Eighth Embodiment)

Figure 18:
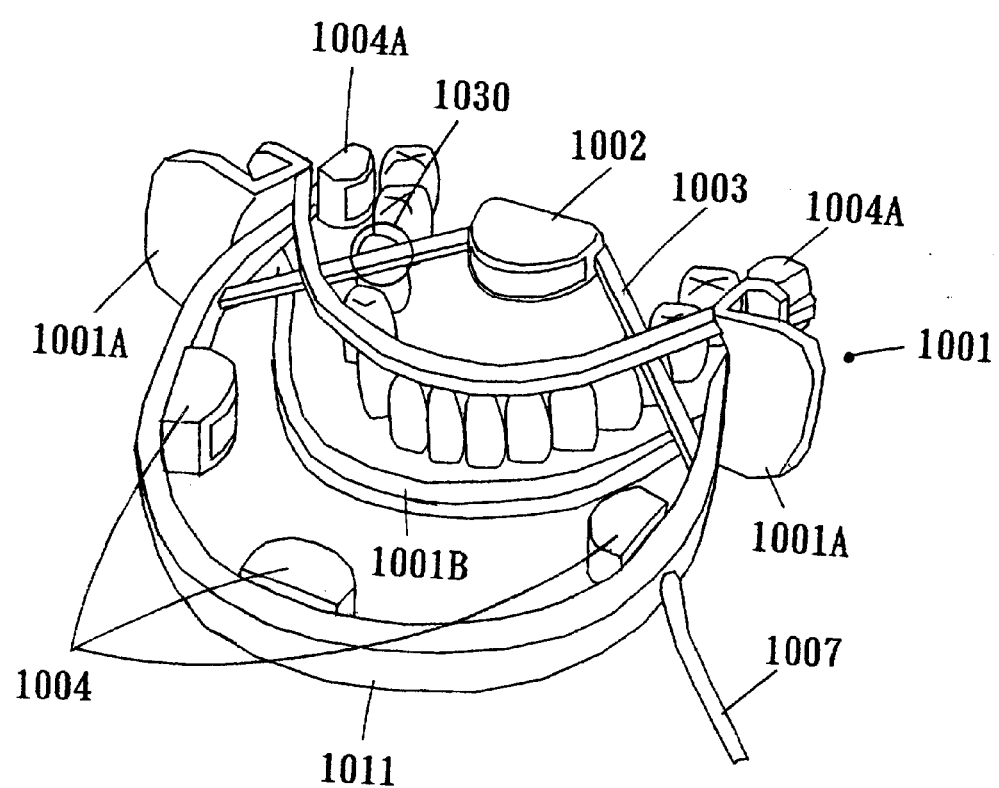
FIG. 18 is an external view showing an oral cavity pickup apparatus according to an eighth embodiment of the present invention.
Figure 19:
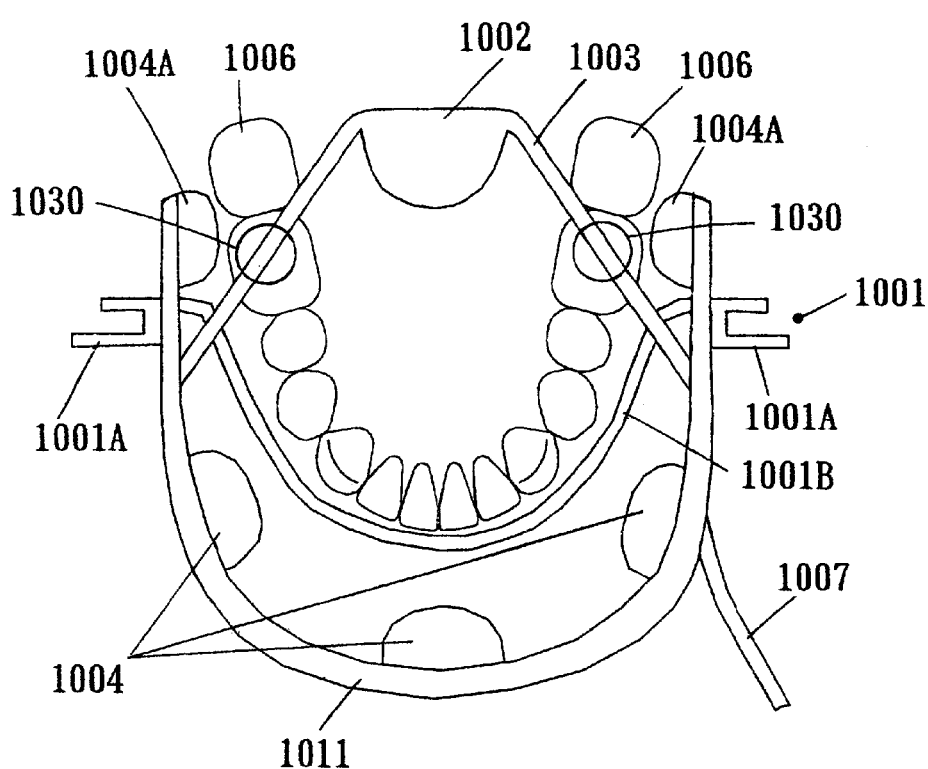
FIG. 19 is a partial cross sectional plan view showing the oral cavity pickup apparatus according to the eighth embodiment of the present invention.
Figure 20:
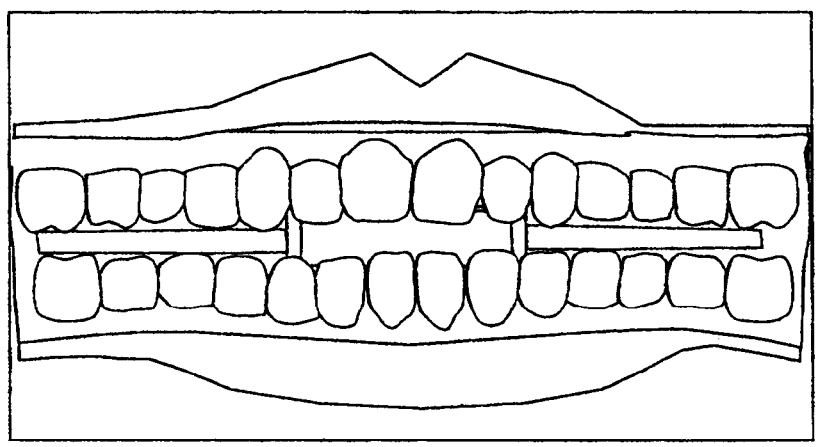
FIG. 20 is an image view showing the exterior of the oral cavity obtained by picking up with the oral cavity pickup apparatus according to the eighth embodiment of the present invention.

FIG. 18 is an external view showing an oral cavity image pickup apparatus according to a eighth embodiment of the present invention, FIG. 19 is a partial cross sectional plan view showing the oral cavity image pickup apparatus and FIG. 20 is an image view showing an image for the exterior of oral cavity obtained by image-picking up by the oral cavity image pickup apparatus.

In FIG. 18, reference numeral 1001 denotes the opener; 1002, the inside image pickup unit; 1003, the intra-oral cavity holding means; 1011, extra-oral cavity holding means in which outside image pickup units 1004A are disposed at both ends of the substantially U-character shape toward the molar 1006 and the milk molar, further the outside image pickup units 1004 are provided for image-picking up the vicinity of a premolar tooth and dogtooth substantially from the front, and a plurality of the outside image pickup units 1004 for image-picking up from the front of the oral cavity are provided. In this respect, the outside image pickup unit 1004A may be provided at a holding piece provided on the inside of the oral cavity from the right and left lip receivers 1001A of the opener 1001 although not shown.

Images obtained by picking up through the use of these plurality of the outside image pickup units 1004 are subjected to a treatment of joining plural image information together through the use of an image processing circuit mounted onto the circuit substrate or the external camera circuit, and can be observed with the dentition arranged in a horizontal direction as shown in FIG. 20.

A cable cord 1007 for transmitting a video output signal, a driving signal or the like from the circuit substrate has been inserted into the extra-oral cavity holding means 1011 and the intra-oral cavity holding means 1003, and is drawn out from the extra-oral cavity holding means 1011. The cable cord 1007 drawn out is connected to the power supply, the external camera circuit, the monitor TV or the like, which are not shown. In this respect, the inside image pickup unit 1002 may be configured by one CCD, or may be configured by plurality of CCDs as described in the seventh embodiment.

According to the intra-oral cavity image pickup apparatus of the present embodiment having such a configuration, it becomes possible to easily pick up the side surface of the front side of the molar or the like located in the depths within the oral cavity. Also, teeth constituting dentition are divided into each group of a plurality of teeth to image-pick up them from substantially the front, whereby overlapping of adjacent teeth is reduced to exclude portions which constitute a dead angle. Thus, the row of teeth, a state of teeth, or the like as viewed from the front can be obtained as one image for the entire mouth instantaneously, and an image as viewed from the back within the oral cavity can be obtained at the same time.

(Ninth Embodiment)

Figure 21:
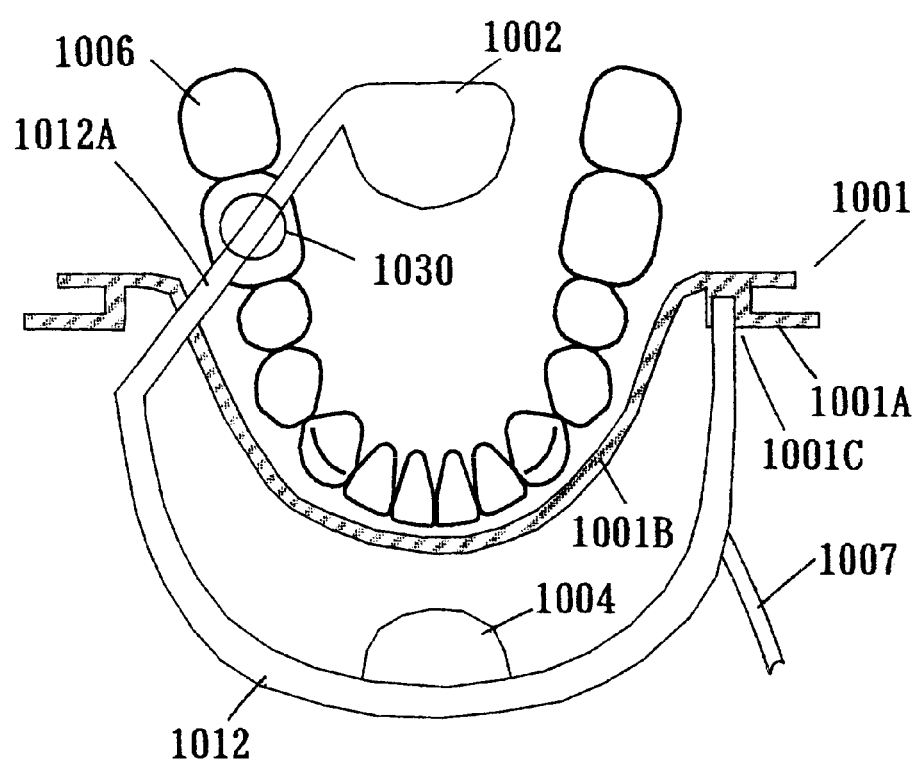
FIG. 21 is a partial cross sectional plan view showing the oral cavity pickup apparatus according to a ninth embodiment of the present invention.
Figure 22:
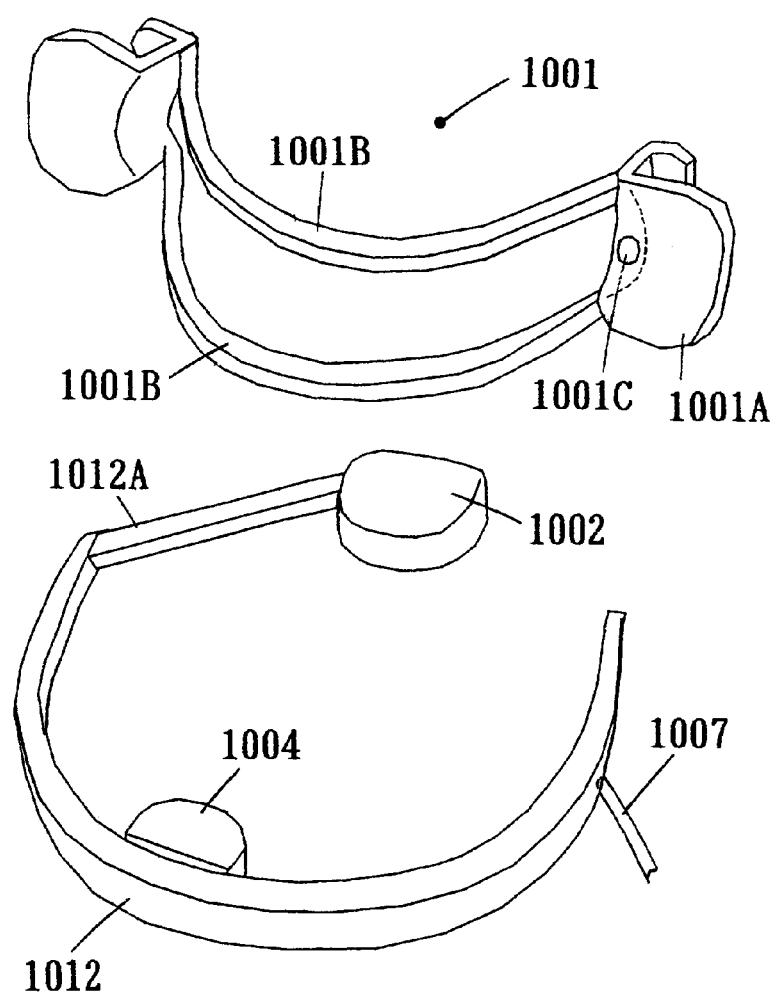
FIG. 22 is an external view showing an oral cavity pickup apparatus according to the ninth embodiment of the present invention.

FIG. 21 is a partial cross sectional plan view showing an oral cavity image pickup apparatus according to a ninth embodiment of the present invention, and FIG. 22 is an external view showing the oral cavity image pickup apparatus.

In FIGS. 21 and 22, reference numeral 1001 denotes the opener; 1002, the inside image pickup unit; 1004, the outside image pickup unit; 1006, the molar: and 1012, substantially U-character shaped image pickup holding means of integrally fixing an intra-oral cavity holding means 1012A for holding the inside image pickup unit 1002 within the oral cavity.

A cable cord 1007 for transmitting a video output signal, a driving signal or the like from the circuit substrate has been inserted into the image pickup holding means 1012 and the intra-oral cavity holding means 1012A, and is taken out from the image pickup holding means 1012. The cable cord 1007 taken out is connected to the power supply, the external camera circuit, the monitor TV or the like, which are not shown.

Right and left lip receivers 1001A of the opener 1001 are provided with mounting holes 1001C for detachably holding this pickup holding means 1012, and intra-oral cavity holding means 1012A of the image pickup holding means 1012 is mounted to be interposed between upper and lower coupling arms 1001B.

According to the intra-oral cavity image pickup apparatus of the present embodiment having such a configuration, since the opener 1001 and the pickup holding means 1012 can be detachably mounted, it becomes possible to replace, and the opener 1001 is mass-produced through the use of means such as resin molding to thereby reduce the cost, and can be used as a disposable member, or the openers are retained in large quantities to thereby restrain frequency in sterilization. Also, a disposable member such as vinyl can be used for the pickup holding means 1012 as an easy-to-mount transparent cover, and this transparent cover is used once and then is thrown away to thereby enable this apparatus to be used hygienically, troubleness of sterilization when a large number of people are observed like dental examination can be eliminated.

These openers 1001 and the pickup holding means 1012 are prepared in various sizes, whereby correspondence to infants to adults can be easily performed.

(Tenth Embodiment)

Figure 23:
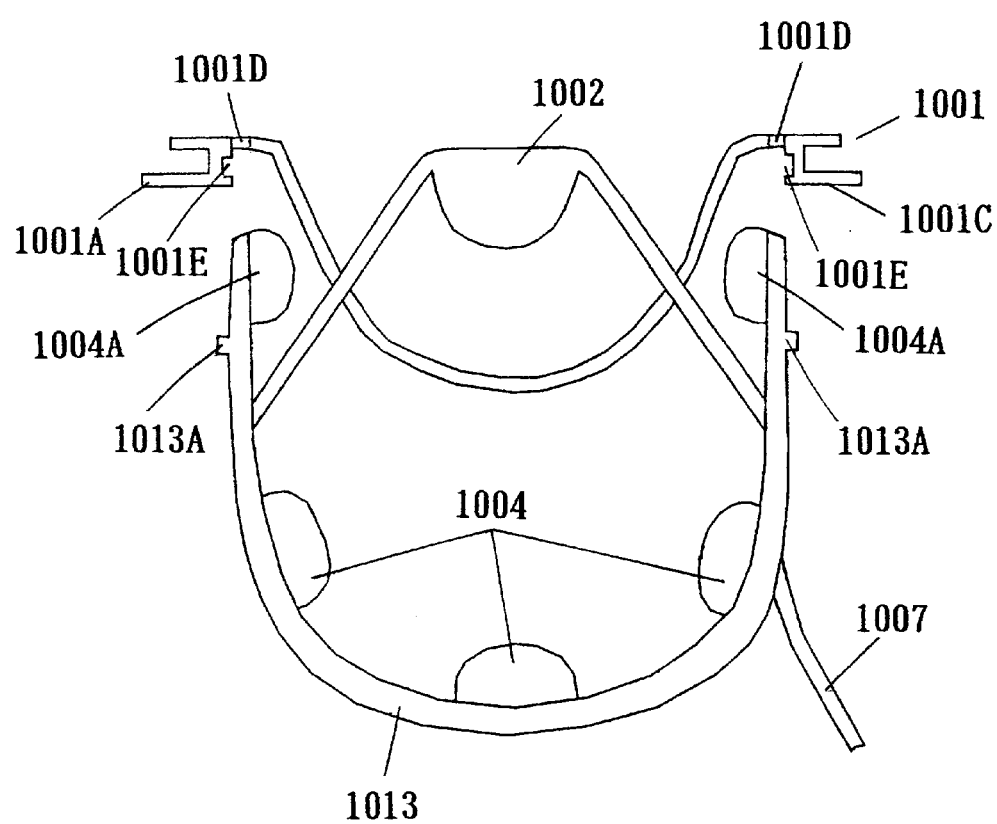
FIG. 23 is a partial cross sectional plan view showing the oral cavity pickup apparatus according to a tenth embodiment of the present invention.

FIG. 23 is a partial cross sectional plan view showing an oral cavity image pickup apparatus according to a tenth embodiment of the present invention. In FIG. 23, reference numeral 1013 denotes substantially U-character shaped extra-oral cavity holding means provided with a plurality of the outside image pickup unit 1004, and intra-oral cavity holding means 1003 of fixing the inside image pickup unit 1002 is integrally fixed.

The inside image pickup unit 1002 and the outside image pickup unit 1004 are hermetically configured, and the fixing portion with the extra-oral cavity holding means 1013 is hermetically configured.

This extra-oral cavity holding means 1013 is made of an elastic body having elasticity when the U-character shape is going to open outward at all times, the both ends of this extra-oral cavity holding means 1013 are held so as to close inward, and the extra-oral cavity holding means 1013 is mounted so as to be interposed between the upper and lower coupling arms 1001B of the opener 1001. At this time, the height position is determined by a stepped portion 1001D of the opener 1001, and if the hand is released when a stopper portion 1013A provided at the extra-oral cavity holding means 1013 is fitted in a stopper receiver 1001E provided in the right and left lip receivers 1001A of the opener 1001, the extra-oral cavity holding means 1013 is going to open with elasticity to thereby be fixed and held, and falling off can be prevented.

A cable cord 1007 for transmitting a video output signal, a driving signal or the like from the circuit substrate has been inserted into the extra-oral cavity holding means 1013 and the intra-oral cavity holding means 1003, and is drawn out from the extra-oral cavity holding means 1013. The cable cord 1007 drawn out is connected to the power supply, the external camera circuit, the monitor TV or the like, which are not shown.

According to the intra-oral cavity image pickup apparatus of the present embodiment having such a configuration, since the opener 1001 and extra-oral cavity holding means 1013, to which the inside image pickup unit 1002 and the outside image pickup unit 1004 are fixed can be detachably mounted, it becomes possible to replace, and the opener 1001 is mass-produced through the use of means such as resin molding to thereby reduce the cost, and can be used as a disposable member, or the openers are retained in large quantities to thereby restrain frequency in sterilization. Also, since the inside image pickup unit 1002, the outside image pickup unit 1004, the extra-oral cavity holding means 1013 or the like are hermetically configured, it is easy to be sterilized and is hygienic.

These openers 1001 and the pickup holding means 1012 are prepared in various sizes, whereby correspondence to infants to adults can be easily performed.

In this respect, in the above described first to sixth embodiments, the description has been made of the intra-oral cavity holding means 7 and the wrong-insertion preventing guard 8 as one having a shape of substantially key-hole as a whole, but the present invention is not limited thereto, and it will suffice if a portion which is exposed outside the oral cavity has such a shape as not to enter the oral cavity. A shape of substantially key-hole is an example of closed curve, and it is not limited thereto, but an iron dumbbell type, a gourd shape or the like may be used. In short, the shape of the holding means according to the present invention will be suffice if it is a closed curve including at least two holding areas in which the holding means is held, and if portions including those two holding areas is in such positional relationship that they are on the same plane, such one as its entire or partial portion is curved within or without the oral cavity may be used.

In each of the above described embodiments, sizes of the intra-oral cavity holding means 1007 and 1003, the extra-oral cavity holding means 1005, 1011 and 1013, and the wrong-insertion preventing guard 1008 may be changed in accordance with the size and shape of the user's mouth. This enables correspondence to a wide range of users including from infants to adults.

An oral cavity pickup apparatus according to the present invention corresponds to an intra-oral cavity image pickup apparatus according to the first to sixth embodiments and an oral cavity pickup apparatus according to the seventh to tenth embodiments, and pickup means according to the present invention corresponds to an image pickup system according to the first to sixth embodiments, holding means according to the present invention corresponds to the image pickup unit holder, the intra-oval cavity holding means, the wrong-insertion preventing guard according to the first to sixth embodiments and a member for cooperating with each of those means, and holding areas according to the present invention correspond to holding areas 60 according to the first to the sixth embodiments and holding areas 1030 according to the seventh to tenth embodiments.

Further, pickup means according to the present invention corresponds to the outside image pickup unit 1004 and the inside image pickup unit 1002 according to the seventh to tenth embodiments, the first holding means according to the present invention corresponds to the intra-oral cavity holding means 1003 according to the seventh to tenth embodiments, the second holding means according to the present invention corresponds to the extra-oral cavity holding means 1005, 1011 and 1013 according to the seventh to tenth embodiments, and dentition exposure means according to the present invention corresponds to the opener 1001 according to the seventh to tenth embodiments.

As described above, according to the present invention, it is possible to realize a simple-to-handle oral cavity pickup apparatus capable of obtaining once a row of teeth, a state of teeth, and a state of gums within the oral cavity as viewed from the back, which is the inside of the oral cavity, and the row of teeth, the state of teeth, and the state of gums as viewed from the front, which is the outside of the oral cavity as an image for the entire mouth respectively only by holding it in the mouth.

What is claimed is:

1. An oral cavity image pickup apparatus, comprising:

image pickup means having at least an object lens and an imaging device; and holding means of holding said image pickup means inside and/or outside an oral cavity, wherein said image pickup means is capable of image-picking up full or partial dentition exposed inside and/or outside said oral cavity and partial bio-tissue at a time, and said holding means includes a first arm for placement inside the oral cavity at least between left molars and right molars of sufficient length corresponding to at least a distance between said left molars and right molars and defining a transverse dimension, said image pickup means being held on at least the first arm between the left and right molars, and a second arm having (1) a first part for placement inside the oral cavity and coupled to the first arm, and (2) a second part being at least of length in the transverse dimension as the first arm and extending from both sides of the oral cavity.

2. An oral cavity image pickup apparatus, comprising:

image pickup means having at least an object lens and an imaging device; and holding means of holding said image pickup means inside and/or outside an oral cavity, wherein said holding means has a first arm for placement inside the oral cavity at least between left molars and right molars of sufficient length corresponding to at least a distance between said left molars and right molars and defining a transverse dimension, said image pickup means being held on at least the first arm between the left and right molars, a second arm having (1) a first part for placement inside the oral cavity and coupled to the first arm, and (2) a second part being at least of length in the transverse dimension as the first arm and extending from both sides of the oral cavity, and a bitten portion which is bitten by upper and lower teeth to thereby stabilize said apparatus, and said image pickup means is disposed inside and/or outside said oral cavity when said bitten portion of said holding means is bitten by said upper and lower teeth.

3. An oral cavity image pickup apparatus, comprising:

a plurality of image pickup means having at least an object lens and an imaging device; and holding means of holding said image pickup means inside and/or outside an oral cavity, said holding means includes a first arm for placement inside the oral cavity at least between left molars and right molars of sufficient length corresponding to at least a distance between said left molars and right molars defining a transverse dimension, said plurality of image pickup means being held on at least the first arm between the left and right molars, and a second arm having (1) a first part for placement inside the oral cavity and coupled to the first arm, and (2) a second part being at least of length in the transverse dimension as the first arm and extending from both sides of the oral cavity, wherein said plurality of image pickup means are disposed in such manner that each of the plurality of image pickup means has a respectively different angle of view.

4. The oral cavity image pickup apparatus according to any one of claims 1 to 3, wherein said image pickup means is capable of image-picking up at a time full or partial dentition belonging to an upper chin, and a portion of bio-tissue and/or full or partial dentition belonging to a lower chin, and a portion of bio-tissue.

5. The oral cavity image pickup apparatus according to any one of claims 1 to 3, wherein said object lens is a fish-eye lens.

6. The oral cavity image pickup apparatus according to any one of claims 1 to 3, wherein said holding means has light projecting means and said light projecting means projects a light upon full or partial dentition exposed within and/or without said oral cavity and partial tissue.

7. The oral cavity image pickup apparatus according to any one of claims 1 to 3, wherein said holding means has dentition exposure means, and in a state in which said image pickup means is capable of image-picking up, at least a portion of said dentition exposure means is disposed at both end portions of lips in such a manner that said lips and a portion of the cheek are pushed open.

8. The oral cavity image pickup apparatus according to any one of claims 1 to 3, wherein said first arm is disposed inside said oral cavity, and said second arm is disposed outside said oral cavity.

9. The oral cavity image pickup apparatus according to claim 8, wherein said first arm and said second arm are integrally fixed.

10. The oral cavity image pickup apparatus according to claim 8, wherein said first arm and said second arm are detachably disposed on said image pickup means.

11. The oral cavity image pickup apparatus according to claim 9, wherein said image pickup means is movably disposed on said holding means.

12. The oral cavity image pickup apparatus according to claim 8, wherein said image pickup means is disposed on said first arm and said first arm is quasi-horse shoe shaped, U-character shaped or V-character shaped.

13. The oral cavity image pickup apparatus according to claim 12, wherein said second arm has a shape of larger width than width of said first arm in a boundary portion with said second arm.

14. The oral cavity image pickup apparatus according to claim 12, wherein said holding means forms a substantially key-hole shape all over said first arm and said second arm.

15. The oral cavity image pickup apparatus according to claim 12, wherein said second arm has a curved shape at a boundary portion between said first arm and said second arm with respect to said first arm.

16. The oral cavity image pickup apparatus according to any one of claims 1 to 3, wherein said image pickup means continuously or intermittently rotates with a predetermined region of said holding means as a base point.

17. The oral cavity image pickup apparatus according to claim 3, further comprising image processing means of joining plural signals from said image pickup means together as one image.

18. The oral cavity image pickup apparatus according to claim 17, further comprising display means capable of selectively displaying each of a signal from said image processing means and plural signals from said image pickup means.

19. The oral cavity image pickup apparatus according to any one of claims 1 to 3, wherein at least one of said first arm and said second arm is made of transparent material or material having permeability.

20. The oral cavity image pickup apparatus according to any one of claims 1 to 3,
wherein said holding means comprises:
driving means of driving said image pickup means;
power supply for supplying electric power to said image pickup means and an image pickup assisting means; and
radio signal output means of outputting a signal image-picked up by said image pickup means.

21. The oral cavity image pickup apparatus according to any one of claims 1 to 3, wherein said image pickup means and said holding means are made integral with each other so as to enable them to be disassembled respectively.

22. The oral cavity image pickup apparatus according to any one of claims 1 to 3, wherein a shape of said holding means is a closed curve including at least two holding areas, in which said holding means is held, as a whole and wherein portions including at least two holding areas of said closed curve are on the same plane.

* * * * *